United States Patent
Paul, Jr.

(10) Patent No.: US 7,158,834 B2
(45) Date of Patent: Jan. 2, 2007

(54) METHOD AND APPARATUS FOR PERFORMING MICROCURRENT STIMULATION (MSC) THERAPY

(75) Inventor: Edward L. Paul, Jr., Wrightsville Beach, NC (US)

(73) Assignee: Atlantic Medical, Inc., Wilmington, NC (US)

( * ) Notice: Subject to any disclaimer, the term of this patent is extended or adjusted under 35 U.S.C. 154(b) by 390 days.

(21) Appl. No.: 10/738,921

(22) Filed: Dec. 17, 2003

(65) Prior Publication Data
US 2004/0176820 A1    Sep. 9, 2004

Related U.S. Application Data

(63) Continuation-in-part of application No. 10/457,857, filed on Jun. 10, 2003.

(60) Provisional application No. 60/388,577, filed on Jun. 13, 2002.

(51) Int. Cl.
*A61N 1/18* (2006.01)
(52) U.S. Cl. ............... 607/48; 607/54; 607/141
(58) Field of Classification Search ........... 607/141, 607/53, 54, 68, 69; 623/4.1, 5.11, 6.63; 606/4
See application file for complete search history.

(56) References Cited

U.S. PATENT DOCUMENTS

| | | | |
|---|---|---|---|
| 793,004 A | 6/1905 | May | |
| 4,018,218 A | 4/1977 | Carlson et al. | |
| 4,712,558 A | 12/1987 | Kidd et al. | |
| 4,989,605 A * | 2/1991 | Rossen | 607/46 |
| 5,099,829 A | 3/1992 | Wu | |
| 5,109,847 A | 5/1992 | Liss et al. | |
| 5,314,423 A | 5/1994 | Seney | |
| 5,324,317 A | 6/1994 | Reiss | |
| 5,397,338 A | 3/1995 | Grey et al. | |
| 5,447,526 A | 9/1995 | Karsdon | |
| 5,522,864 A * | 6/1996 | Wallace et al. | 607/53 |
| 5,549,656 A | 8/1996 | Reiss | |
| 5,571,150 A | 11/1996 | Wernicke et al. | |
| 5,611,350 A | 3/1997 | John | |
| 5,702,428 A | 12/1997 | Tippey et al. | |
| 5,713,940 A | 2/1998 | Karsdon | |
| 5,800,458 A | 9/1998 | Wingrove | |
| RE35,987 E | 12/1998 | Harris et al. | |

(Continued)

OTHER PUBLICATIONS

Letter from Dr. Joel S. Rossen to Dr. Edward L. Paul, inventor of the present invention.

(Continued)

*Primary Examiner*—Robert E. Pezzuto
*Assistant Examiner*—Brian T. Gedeon
(74) *Attorney, Agent, or Firm*—Gardner Groff Santos & Greenwald P.C.

(57) ABSTRACT

A method and apparatus for providing microcurrent stimulation (MSC) therapy. In accordance with the present invention, it has been determined that the application of microcurrent signals at particular frequencies to the eye for particular periods of time stabilizes and even improves conditions of macular degeneration and other ocular diseases. Experimental data from clinical trials shows that results of persons who underwent therapy are at least better than placebo (i.e., efficacious), and that the therapy is safe. In fact, experimental data from clinical trials showed that approximately 98% of the patients who underwent the MCS therapy of the invention experienced either stabilization or improvement of macular degeneration within one year of starting therapy. Of this percentage, approximately 65% of the patients subjected to the MCS therapy experienced improved vision, while approximately 32% experienced stabilization of macular degeneration (i.e., no further loss of vision).

3 Claims, 8 Drawing Sheets

U.S. PATENT DOCUMENTS

| | | | |
|---|---|---|---|
| 5,851,223 | A | 12/1998 | Liss et al. |
| 5,935,156 | A | 8/1999 | Chandler et al. |
| 5,964,789 | A | 10/1999 | Karsdon |
| 6,035,236 | A * | 3/2000 | Jarding et al. ............ 607/53 |
| 6,066,163 | A | 5/2000 | John |
| 6,219,578 | B1 | 4/2001 | Collins et al. |
| 6,275,735 | B1 | 8/2001 | Jarding et al. |
| 6,393,319 | B1 | 5/2002 | Bock et al. |
| 6,445,955 | B1 | 9/2002 | Michelson et al. |
| 2005/0137649 | A1* | 6/2005 | Paul, Jr. .................. 607/53 |
| 2005/0209656 | A1* | 9/2005 | Chen et al. ............... 607/54 |

OTHER PUBLICATIONS

U.S. FDA Document relating to Dr. Joel S. Rossen's invention described in the letter.

Michael et al., "Nutritional Supplementation, Electrical Stimulation and Age Related Macular Degeneration," Journal of Orthomolecular Medicine, vol. 8, No. 3, 1993, pp. 168-171.

Allen et al., "Macular Degeneration Treatment with Nutrients and Micro Current Electricity," Journal of Orthomolecular Medicine, 4th Quarther 1998, vol. 13, No. 4.

Michael et al., "Nutritional Supplementation, Electrical Stimulation and Age Related Macular Degenaration," Indiana School of Optometry.

Paul May, "Adenosie Triphosphate—ATP," Bristol University.

Cheng et al., "The Effects of Electrical Currents on ATP Generation, Protein Synthesis, and Membrane Transport in Rat Skin," Clinical Orthopedics and Related Research, No. 171, Nov.-Dec. 1982, pp. 264-272.

Feher et al., "Mitotropic Compounds for the Treatment of Age Related Macular Degeneration, The Metabolic Approach and a Pilot Study," Ophthalmologica 2003:217, pp. 351-357.

Optogon Corporation, "Making Microcurrent Stimulation Avaiable to the Victims of Macular Degeneration," http://www.optogon.com.

Micro Stim, "Transcutaneous Electrical Nerve Stimulation System, LED (Light Emitting Diode) Electrode System," Patient and Clinician Instruction Manual, pp. 1-13.

Carley et al., "Electrotherapy for Acceleration of Would Healing: Low Intensity Direct Current," Arch Phys Med Rehabil, vol. 66, Issue 7, Jul. 1985, pp. 443-446.

Wolcott et al., "Accelerated Healing of Skin Ulcers by Electrotherapy: Preliminary Clinical Results," Southern Medical Journal, vol. 62, Issue 7, Jul. 1969, pp. 795-801.

Gault et al., "Use of Low Intensity Direct Current in Management of Ischemic Skin Ulcers," Physical Therapy, vol. 56, No. 3, Mar. 1976, pp. 265-269.

Nessler et al., "Direct-Current Electrical Stimulation of Tendon Healing in Vitro," Clinical Orthopaedics and Related Research, No. 217, Apr. 1987, pp. 303-312.

Owoeye et al., "Low-Intensity Pulsed Galvanic Current and the Healing of Tenotomized Rat Achilles Tendons: Preliminary Report Using Load-to Breaking Measurements," Archives of Physical Medicine and Rehabilitation, vol. 68, No. 7, Jul. 1987, pp. 415-418.

Altman, L.K., "Cell Channel Finding Earns Nobel Prize: Two Germans Found How Cells Control Their Electrical State," New York Times, Oct. 8, 1991, pp. C1, C3: Science Times Section.

Richez, et al., "Bone Changes Due to Pulses of Direct Electrical Microcurrent," Virchows ArchivA: Pathology, Pathologische Anatomie, vol. 357, No. 1, 1972, pp. 11-18.

Byl et al., "Pulsed Microamperage Stimulation: A Controlled Study of Healing of Surgically Induced Wounds in Yucatan Pigs," Physical Therapy, vol. 74, No. 3, Mar. 1994, pp. 201-218.

Bertolucci et al., "Clinical Comparative Study of Microcurrent Electrical Stimulation to Mid-Laser and Placebo Treatment in Degenerative Joint Disease of the Temporomandibular Joint," Journal of Craniomandibular Practice, vol. 13, No. 2, Apr. 1995, pp. 116-120.

Wing, Thomas W., M.D., "Can ELF Help Your Patients?" Chiropractic Economics, Mar./Apr. 1987.

* cited by examiner

Fig. 6

METHOD AND APPARATUS FOR PERFORMING MICROCURRENT STIMULATION (MSC) THERAPY

CROSS-REFERENCE TO RELATED APPLICATIONS

This application is a continuation-in-part of application Ser. No. 10/457,857, which was filed on Jun. 10, 2003, entitled "TRANSCUTANEOUS ELECTRICAL NERVE STIMULATION DEVICE AND METHOD USING MICROCURRENT", which is incorporated by reference herein in its entirety, which claims priority to U.S. provisional application Ser. No. 60/388,577, which was filed on Jun. 13, 2002, entitled "TRANSCUTANEOUS ELECTRICAL NERVE STIMULATION DEVICE AND METHOD USING MICROCURRENT".

TECHNICAL FIELD OF THE INVENTION

The present invention relates to a method and apparatus for performing microcurrent simulation (MSC) therapy. More particularly, the present invention relates to applying micro-amperage current (microcurrent) to the eye at different frequencies for particular periods of time to effectuate stabilization or improvement of macular degeneration and other ocular diseases.

BACKGROUND OF THE INVENTION

Microcurrent Stimulation (MCS) therapy is a noninvasive procedure that involves stimulating the retina and nerve fibers with very low intensity electrical current using a Food and Drug Administration (FDA) approved electrical stimulation device. It is theorized that MCS Therapy works by increasing intracellular ATP (adenosine triphosphate) concentrations, enhancing protein synthesis, and stimulating the cells ability to absorb nutrients. Through these mechanisms, MCS therapy improves RPE (retinal pigment epithelium) efficiency and thereby may restore and/or improve retinal function.

Cheng, et al. disclosed increasing ATP levels from 300% to 500% through electrostimulation of the rat tissue with current levels from 50 to 1,000 μA. "The Effects of Electrical Currents on ATP Generation, Protein Synthesis, and Membrane Transport", *Clinical Orthopaedics and Related Research*, No. 171, November–December, 1982.

ATP is synthesized in the mitochondria process known as the Kreb's Cycle, the sequence of reactions in the mitochondria that complete the oxidation of glucose in respiration. Kroll and Guerrieri have shown that there are age related changes in mitochondrial metabolism resulting in a decrease of the ATP synthase activity in the retina with age. Guerrieri has gone further to show functional and structural differences of the mitochondria F0F1 ATP synthase complex in aging rats. It is theorized that many retinal diseases, at least in part, are due to a decrease in mitochondria function and the subsequent decrease in intracellular ATP. This decrease in mitochondria function results from free radical damage and the mutation of mitochondria DNA (mtDNA). It is interesting to note the genetic link between ATP and retinal disease. ATP Synthase (ATPase) is an enzyme which catalyzes the synthesis of ATP. A genetic defect in the ATPase 6 Gene has now been implicated in retinitis pigmentosa.

A variety of devices and procedures are used to perform MCS therapy. For example, U.S. Pat. No. 5,522,864 proposes that macular degeneration or other ocular pathology may be treated by placing a positive electrode of a direct microcurrent source in contact with the closed eyelid of the subject and placing a negative electrode away from the eye of the subject, preferably on the neck of the subject. These electrodes apply a constant direct current of 200 microamps for approximately 10 minutes.

U.S. Pat. No. 6,275,735 discloses a method and apparatus for applying a microcurrent signal to a body part to combat visual system diseases such as macular degeneration. A controller outputs data words to a digital-to-analog converter (DAC), which produces analog electrical signals that are provided to a voltage controlled oscillator (VCO). The VCO generates electrical signals having frequencies that depend on the signals received from the DAC. The user holds an electrical probe to a body part to be treated and a microcurrent signal having the frequency produced by the VCO is applied via the probe to the body part. The first data word causes a first relatively low frequency (0 to 400 Hz) microcurrent signal to be applied and a second data word causes a second relatively high frequency (500 to 2 MHz) microcurrent signal to be applied.

While many attempts have been made to use MCS therapy to treat macular degeneration and other ocular diseases, existing methods and apparatuses proposed for this purpose have, to date, been ineffective. Accordingly, a need exists for an effective approach to MCS therapy that enables conditions of macular degeneration and other ocular diseases to be improved or at least stabilized.

SUMMARY OF THE INVENTION

The present invention provides a method and apparatus for performing MCS therapy. In accordance with the present invention, it has been determined that the application of microcurrent signals at particular frequencies to the ocular tissue for particular periods of time stabilizes and even improves conditions of macular degeneration and other ocular diseases. The application of microcurrent to the ocular tissue results in an increase in ATP levels in the ocular tissue. Experimental data from clinical trials shows that results of persons who underwent therapy are at least better than placebo, and that the therapy is safe. Therefore, the present invention meets the Federal Food and Drug Administration (FDA) requirements of safety and efficacy.

In fact, experimental data from clinical trials showed that approximately 97% of the patients who underwent the MCS therapy of the invention experienced either stabilization or improvement of macular degeneration within one year of starting therapy. Of this percentage, approximately 65% of the patients subjected to the MCS therapy experienced improved vision, while approximately 32% experienced stabilization of macular degeneration (i.e., no further loss of vision). As few as 3% of the patients experienced no improvement in vision, although the therapy resulted in no harmful effects. Most improvement or stabilization results occurred within six months.

The term "improvement", as that term is used herein, means that the patient was able to read two more lines on the standard Snellen eye chart than the patient was able to read prior to therapy. The term "stabilization", as that term is used herein, means that the patient did not experience any further loss of vision, which is the normal course of macular degeneration.

In accordance with the invention, at least two microcurrent signals that are different in modulation frequency are applied to ocular tissue for particular periods of time. The term "modulation frequency" denotes the beat frequency that is superimposed onto the carrier frequency, which preferably is between 10,000 and 20,000 Hz. The term ocular tissue, as that phrase is used herein, denotes the eye, the eyelid, ocular fluids, and dermal tissue within 5 centimeters (cm) of the eye. A first microcurrent signal at a first modulation frequency is applied to the ocular tissue for a first period of time, after which at least a second microcurrent signal at a second modulation frequency, which is lower than the first modulation frequency, is applied to the ocular tissue for a second period of time. The second period of time is greater than the first period of time. It has been determined that as the modulation frequency of the microcurrent signal decreases, the duration of the time period during which the signal is applied should be increased.

In accordance with the preferred embodiment, at least three, but preferably four, different microcurrent signals are applied to the ocular tissue in a particular sequence in which each subsequently applied signal in the sequence is lower in frequency than the previously applied signal. In accordance with this embodiment, each signal is applied for a longer period of time than the previously applied signal.

One particular sequence that has produced excellent results is as follows. A first microcurrent signal having a first modulation frequency more than 200 Hz but less than or equal to 300 Hz is applied for a period from 1 second up to 120 seconds. A second microcurrent signal having a second modulation frequency more than 10 Hz but less than or equal to 200 Hz is then applied for a period from 1 second up to 240 seconds. A third microcurrent signal having a third modulation frequency more than 1 Hz but less than or equal to 10 Hz is then applied for a period from 10 seconds up to 800 seconds. A fourth microcurrent signal having a fourth modulation frequency greater than 0.1 Hz but less than or equal to 1 Hz is then applied for a period from 10 seconds up to 500 seconds.

Other features and advantages of the invention will become apparent from the following description, drawings and claims.

DETAILED DESCRIPTION OF THE INVENTION

As stated above, the MCS method and apparatus of the present invention have produced very good results, which, prior to the invention, were unobtainable. The patients were subjected to the MCS therapy of the invention for six months, twice a day. Below is a table showing the results for several patients who underwent the therapy. From left to right, the first column in the table lists the patients' identifiers. The second column corresponds to the patients' visual acuity in the right eye prior to therapy. The third column corresponds to the patients' visual acuity in the left eye prior to therapy. The fourth column corresponds to the patients' visual acuity in the right eye post therapy. The fifth column corresponds to the patients' visual acuity in the left eye post therapy. The sixth column corresponds to percent improvement of vision in the right eye. The seventh column corresponds to percent improvement of vision in the left eye.

TABLE 1

| Patient | Start | | End | | % Change | |
| --- | --- | --- | --- | --- | --- | --- |
| ID | R 20/ | L 20/ | R 20/ | L 20/ | R | L |
| TB | 80 | C | 60 | C | 25% | 0% |
| JLC | 200 | 100 | 125 | 50 | 38% | 50% |
| JHC | 30 | 40 | 25 | 30 | 16% | 25% |
| PC | 30 | 50 | 16 | 30 | 47% | 40% |
| DE | 200 | 40 | 160 | 30 | 20% | 25% |
| RE | 125 | 80 | 125 | 80 | 0% | 0% |
| JDF | 60 | 80 | 50 | 80 | 16% | 0% |
| JEF | 400 | 240 | 240 | 120 | 40% | 50% |
| EJ | C | 160 | C | 100 | 0% | 37% |
| MH | 80 | 160 | 60 | 100 | 25% | 37% |
| WH | 160 | 100 | 200 | 60 | −25% | 40% |
| FH | 280 | 300 | 240 | 240 | 14% | 20% |
| EH | 25 | 25 | 25 | 25 | 0% | 0% |
| HH | 240 | 360 | 240 | 240 | 0% | 33% |
| JM | 50 | 40 | 50 | 40 | 0% | 0% |
| GM | 30 | 100 | 20 | 80 | 33% | 20% |
| WH | 50 | 30 | 30 | 25 | 40% | 16% |
| MB | 160 | 40 | 125 | 30 | 22% | 25% |
| JP | 100 | 160 | 100 | 160 | 0% | 0% |

| | |
| --- | --- |
| Improved | 65% |
| Stable | 32% |
| Decreased | 3% |
| Total | 100% |

It can be from the table that an overwhelming majority of patients, 65%, experienced improved vision as a result of the MCS therapy. A large number of the patients, 32%, who did not experience improvement at least experienced stabilization of macular degeneration. Only a very small number of patients, 3%, did not experience improvement or stabilization.

The improvement or stabilization is believed to be the result of an increase in intracellular ATP concentration levels. Cells need to have a minimum ATP concentration level or they will die. ATP concentration levels decrease with aging, and especially with diseases such as macular degeneration. An "increase" in ATP, as that term is used herein, means that the cell has been stimulated with a microcurrent to the point that the cell will function better. Although the stimulation also affects protein synthesis, the ATP concentration level can be a good indicator of how much improvement has occurred. Experimentation with the method and apparatus of the present invention has shown that using a microcurrent in the range of from approximately 100 µA to approximately 1,000 µA provides very good results, with increases ranging from approximately 400% to at least 700%. The experimentation also showed that as currents increased beyond 1,000 µA, the percentage increase in ATP levels declined and ultimately decreased.

Figure 1:
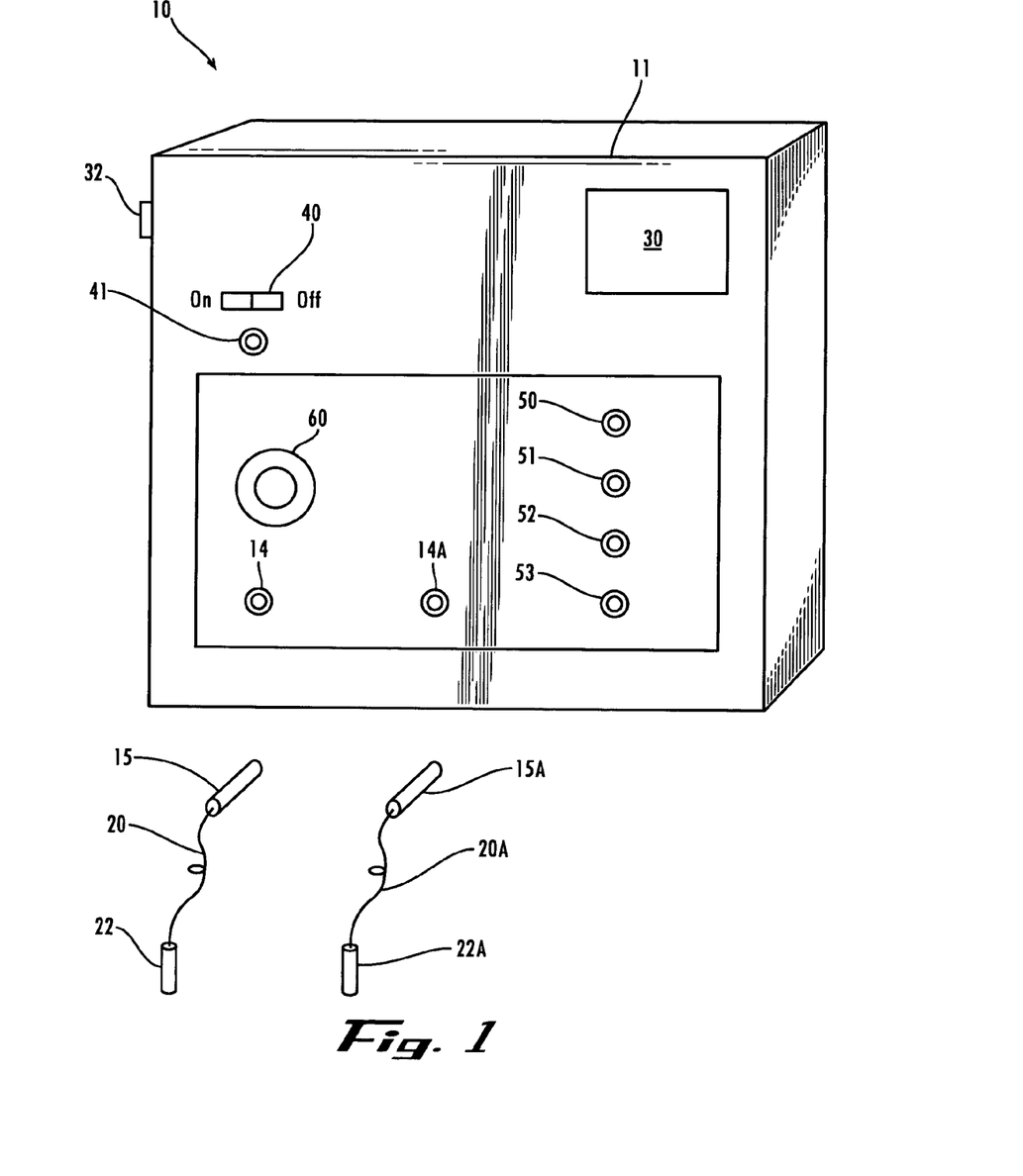
FIG. 1 is a front perspective view of the microcurrent stimulation apparatus in accordance with an embodiment of the present invention.

FIG. 1 shows the microcurrent stimulation apparatus (10) of the invention in accordance with an embodiment. Various components and controls of the apparatus (10) are housed in a box (11). Connected to the box (11) are at least two electrodes (22) and (22A) that provide the microcurrent generated by the microcurrent generation circuitry (FIGS. 4–5B) comprised in the box (11) to the user during therapy. If the polarity of the current is reversed as part of a therapy method, then more than two electrodes may be employed. Electrodes (22) and (22A) connect by means of dual-lead wires (20) and (20A) and probes (15) and (15A) to electrode jacks (14) and (14A) in the front of the box (11). Electrodes (22) and (22A) will be applied to a user completing an electrical circuit, which allows a microcurrent to pass from one electrode through the body of the user to the other electrode to complete the circuit. In accordance with an embodiment, electrodes (22) and (22A) are incorporated into electrode pads, as described below with reference to FIG. 2.

Preferably, within the box (11) are control circuitry and microprocessors, which may be programmed to provide particular types of current in particular waveforms, as will be described below in detail with reference to FIGS. 4–5B. On the front of the box (11) is a turn dial control knob (60) that controls the amount of current passing through the electrodes (22) and (22A) and from jacks (14) to (14A) or vice versa. There is a slide on/off switch (40) and an indicator light (41) that indicates when the microcurrent nerve stimulation apparatus is operating. Ordinarily, batteries will supply the power, which are contained in the battery unit (30) on the front of the box (11). Alternatively, a direct current to power the MCS apparatus (10) may be supplied through the power jack (32), which is shown located on the side of the box (11). When the indicator (41) is dim or not on, it means that the batteries (30) are low and need replacing or that no power is being supplied through the power jack (32). Disposed on the right-hand side of the box (11), from the viewer's perspective, are four program indicator lights (50, 51, 52, 53).

To use the MCS apparatus (10), the user will ordinarily apply the electrodes (22) and (22A) to a prescribed place as determined by a health care provider. The leads (15) and (15A) will be connected to the input jacks (14) and (14A). The on/off switch (40) will turn the apparatus on and the control knob (60) will be adjusted by a user to the appropriate amount of current. This manual adjustment by the user is optional because these functions may instead be performed automatically through appropriate hardware and/or software. Typically, a user will turn the control knob (60) to a level of current where a mild tingle indicating electrical current will be felt, then the control knob (60) will be adjusted downward to reduce the amount of current to where the current is no longer a perceptible tingle to a user. The MCS apparatus (10) will then begin to follow a pre-programmed sequence in which current will be provided with a particular frequency and waveform.

In the preferred program, current will be provided in a square waveform at a frequency of 292 Hz for 60 seconds. During those 60 seconds the program indicator light (50) is lit, which advises the user that the program is underway. When the current applied at 292 Hz for 60 seconds stops, an audible tone will sound and the next step in the therapy program will begin. Here, program indicator light (51) will light, current will be provided at 30 Hz for 120 seconds. At the conclusion of this step in the therapy program, a tone will sound again. The program indicator light (51) will dim and program indicator light (52) will light. This indicates that current will be provided at 9.1 Hz for 180 seconds. A third tone will sound indicating that step in the therapy program is over. Program indicator light (52) will dim and program indicator light (53) will light up. Current will be provided for 0.3 Hz for 360 seconds. At the conclusion of this therapy, a tone will again sound and the microcurrent nerve stimulation apparatus (10) will stop the therapy program. During the therapy program the polarity of the electrodes (22) and (22A) will reverse every two seconds. At this point, a user will remove the electrodes (22) and (22A), turn the on/off switch (40) to off, and the microcurrent nerve stimulation apparatus (10) is ready to begin another treatment program or maybe stored until required for further use.

Figure 2:
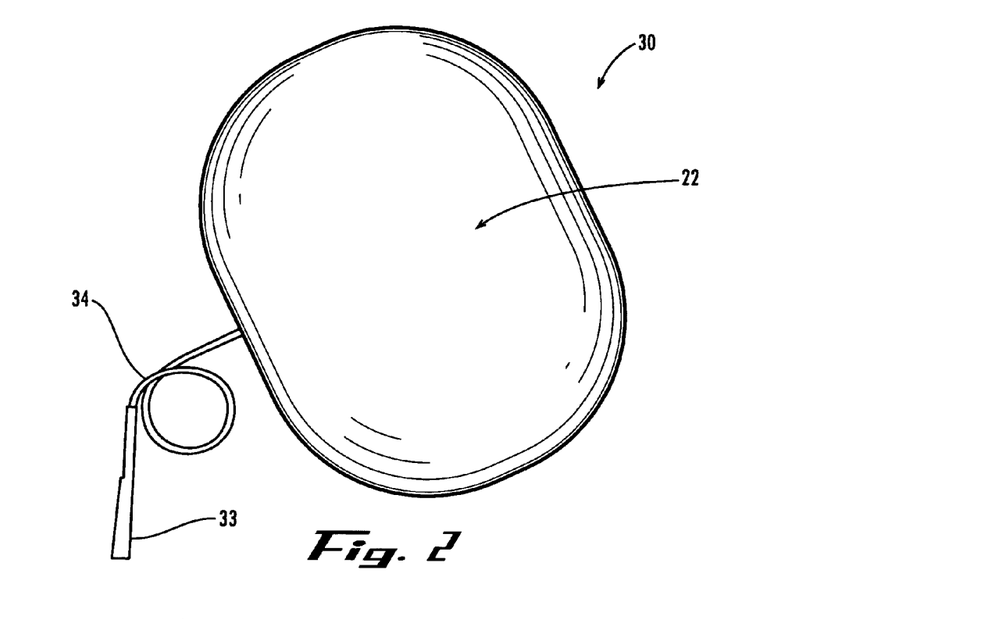
FIG. 2 is a plan view of the electrode pad in accordance with an embodiment of the present invention that is placed in contact with a user's eyelid in order to apply a microcurrent to the user's ocular tissue through the eyelid.

FIG. 2 is a top view of one of the electrode pads (30) that may be used to apply microcurrent to a user's ocular tissue through the eyelid. The user places the electrode pad (30) on the closed eyelid. Prior to placing the pad (30) on the closed eyelid, the user should first prepare the appropriate skin area by careful washing and drying to remove skin oils, cosmetics, or other foreign materials from the skin surface. Preferably, the user places one electrode pad (30) in contact with the left eyelid and one in contact with the right eyelid for bilateral therapy. One of the electrode pads (30) connects to the positive lead wire of dual-lead wire (20), which is connected electrode input jack (14). The other electrode pad (30) connects to the positive lead wire of dual-lead wire (20A), which is connected to electrode input jack (14A).

The positive lead wire (not shown) of dual-lead wire (20) is attached to a pigtail (33), which is connected by the end (34) of the positive lead wire to the electrode pad that covers the left eyelid. The positive lead wire of dual-lead wire (20A) is attached in the same manner to the electrode pad that covers the right eyelid. The negative lead wire (not shown) of dual-lead wire (20) is attached in like manner to an electrode pad (not shown) that is similar or identical to electrode pad (30). This other electrode pad having the negative lead attached to it is placed in contact with the user's skin at some other location on the user's body, such as the back of the user's hand or behind the neck. Likewise, negative lead wire of dual-lead wire (20A) is attached to an electrode pad (not shown) that is similar or identical to electrode pad (30), and which is placed in contact with the user's skin at some other location on the user's body, such as the back of the user's other hand or behind the neck.

The electrode pad (30) preferably has a plastic, rubber or cloth backing secured to it with some type of adhesive. The end (34) of the lead wire attached to the pad is sandwiched between the backing and the pad itself to prevent the lead from being separated from the pad. The electrode pad (30) is made of a conductive material such as, for example, silver, silver chloride, carbon or a combination of carbon and silver. Of course, a variety of different types of conductive materials may be used for this purpose. The pad (30) preferably is attached to the eyelid using a conductive gel, although other attachment materials or devices may be used for this purpose. The electrode pad (30) may be disposable or reusable. The present invention is not limited to any particular configuration or material for the electrode pad (30).

Figure 3A:
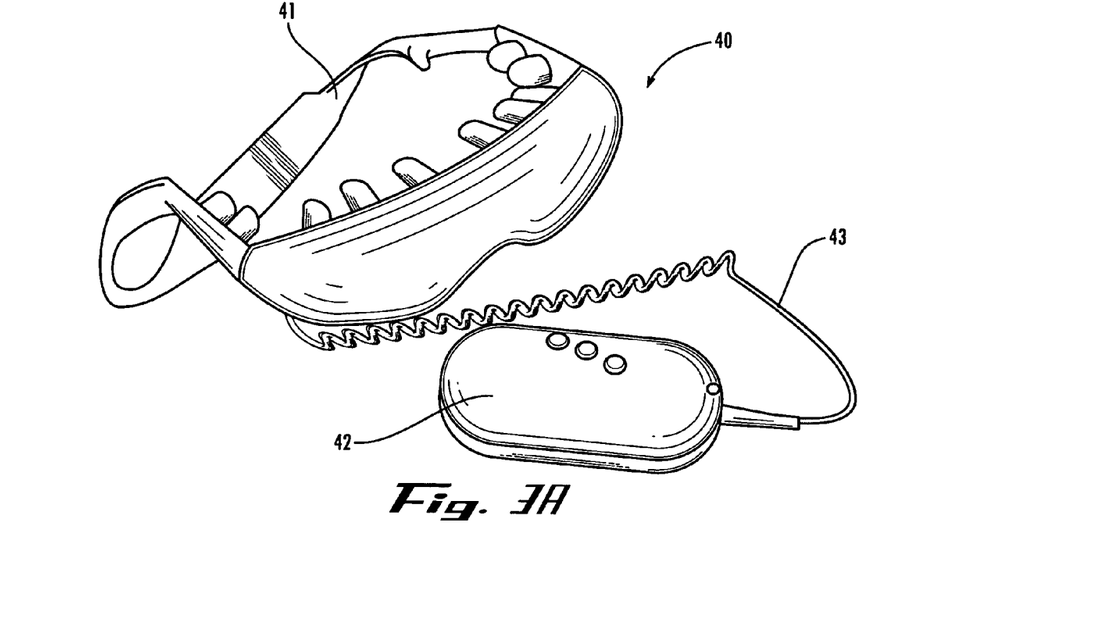
FIGS. 3A–3C are pictorial representations of MCS goggles in accordance with an embodiment of the present invention that are worn by the user in order to apply a microcurrent to the user's ocular tissue through the periorbital region around the eye.
Figure 3B:
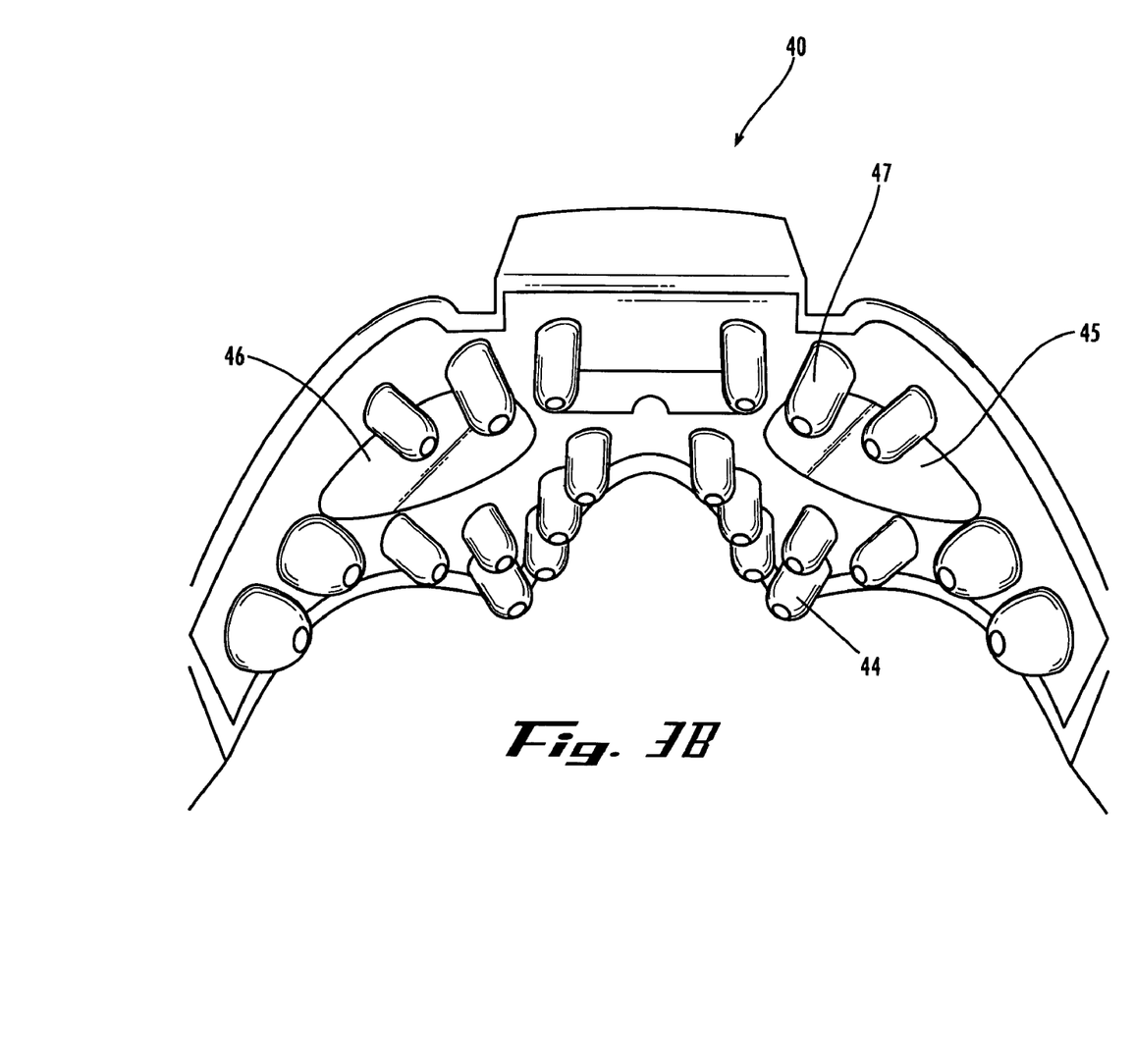
Figure 3C:
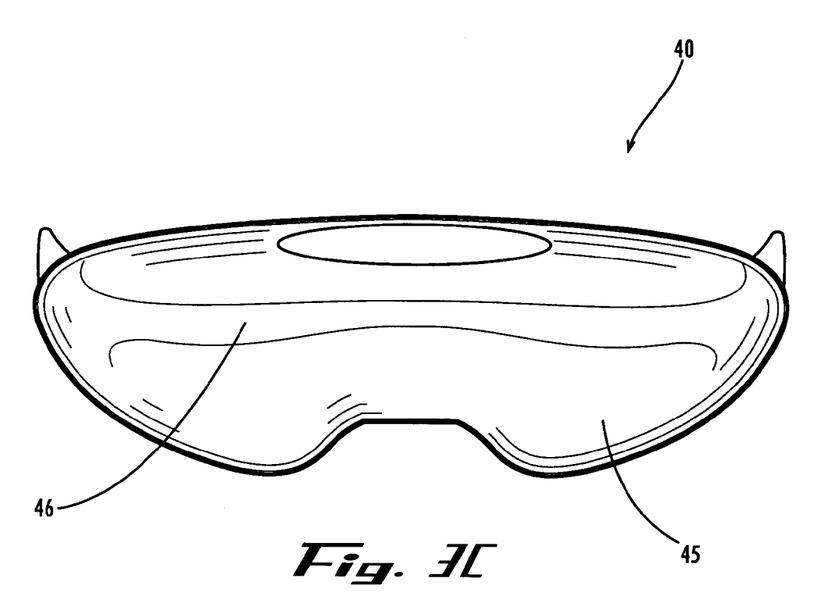

FIGS. 3A–3C illustrate various views of the MCS apparatus of the present invention in accordance with another embodiment. In accordance with this embodiment, the microcurrent is provided to the user's ocular tissues by goggles to which the electrodes are connected. FIG. 3A shows the MCS components, which include plastic goggles (40), an elastic band (41) for providing a force that holds the goggles in place when worn by the user, a casing (42) that houses the MCS electrical components, and a cable (43) that supplies the current generated by the electrical components in casing (42) to the electrodes in the goggles (40). The cable (43) will encase two dual-lead wires of the type described above with reference to FIG. 2. The positive lead wires will have ends disposed in the goggles to couple the microcurrent to the ocular tissue associated with the left and right eyes. The negative lead wires will be connected in some appropriate fashion to some other place on the user's body.

FIG. 3B is a rear plan view of the goggles (40). For each eye, the electrodes (44), which preferably are made from carbon, are arranged in a pattern having shape that matches or closely approximates that of the periorbital region of the face. In accordance with this embodiment, the goggles have small openings formed in them to create see-through regions (45) and (46). This allows the user to be able to see during therapy. With the electrode pad (30) shown in FIG. 2, some users may feel discomfort in not being able to see during therapy. The mesh regions (45) and (46) eliminate this problem. In addition, the regions (45) and (46) provide a further advantage of enabling users to perform other tasks during therapy.

Ends of the electrodes (44) come into contact with the user's skin at a location in the periorbital region of the face. The electrodes (44) are surrounded by a plastic dielectric material (47) that insulates the electrodes (44). FIG. 3C shows a front view of the goggles (40). The regions (45) and (46) are seen in the front views as groups of very small openings formed in the goggles (40). The electrical circuitry housed in casing (42) may be the same as those contained in housing (11) shown in FIG. 1, although a variety of other circuits can be used for the same purpose. The electrical circuitry will be described below with reference to FIGS. 4–5B. It should also be noted that the microcurrent generation circuitry and controller logic could be part of the goggles 40 rather than held in a separate casing (42). In addition, a plurality of electrodes (44) for each eye is not necessary, and it is not necessary that they be configured in a periorbital pattern. A respective single electrode could be used to apply current to the ocular tissue associated with each eye region, either to the closed eyelid or to some other ocular tissue.

Once the electrode pads have been placed in contact with the user's eyelids, if the microcurrent nerve stimulation apparatus (10) is not already on, the control switch (40) is turned on and the intensity knob is adjusted to a preset intensity value on the intensity knob, typically '8'. Then, the knob will be individually adjusted by a user to that user's comfort level according to a set of instructions provided with the unit. Preferably, only current in a predetermined microamperage is applied. Alternatively, the current can be present at a constant dc current of between, for example, 1.0 and 1,000.00 µA.

The manner in which the present invention is used for macular degeneration therapy will now be described with reference to an exemplary embodiment. In accordance with this embodiment, the microcurrent nerve stimulation apparatus (10) is programmed to deliver 12 minutes of macular degeneration therapy. The microcurrent nerve stimulation apparatus (10) preferably is also programmed to audibly notify a user as the therapy proceeds at each stage, although audible notification is optional. For macular degeneration therapy, preferably a first microcurrent is applied at a frequency of 292 Hz with a square waveform for 60 seconds. The amperage output preferably will be no more than 999 microamps. When the 60-second application at 292 Hz is complete, preferably a first beep will sound. The microcurrent nerve stimulation apparatus (10) preferably will automatically start a second microcurrent stimulation at 30 Hz for 120 seconds. Typically, the amount of amperage will not be adjusted and will remain constant throughout the treatment. When the 120-second application is complete, a second audible tone will sound and the third period of microcurrent stimulation will begin automatically.

During the third period, the microcurrent nerve stimulation apparatus (10) applies a 9.1 Hz frequency microcurrent at 180 seconds. Preferably, a third tone will sound at the end of this period and the microcurrent nerve stimulation apparatus (10) will start a fourth period at a frequency of 0.3 Hz for 360 seconds. At the completion of this fourth period, a fourth tone will sound, which will also notify the user that the therapy is complete. During the macular degeneration therapy, the microcurrent nerve stimulation apparatus (10) preferably will reverse the polarity of the electrodes every two seconds. If a user experiences discomfort during the therapy session, the intensity knob (60) may be adjusted downward to a position where the user will no longer experience discomfort. The therapy is ordinarily administered twice a day—once in the morning and once in the evening. It has been found in practice that stimulating with a square waveform for the intervals and frequencies described above is effective for macular degeneration therapy. The term "therapy", as that term is used herein, corresponds to treatment to stabilize or improve conditions of macular degeneration.

It should be noted that the present invention is not only directed toward stabilizing or improving conditions of macular degeneration, but also to stabilizing or improving other ocular diseases or problems, including, for example, Dry Macular Degeneration, Wet Macular Degeneration Stargardt's, Retinitis Pigmentosa, Glaucoma, CMV-Retinitis, Best's Disease Macular Dystrophy, Optic Neuritis, Diabetic Retinopathy, Ischemic Anterior Optic, Neuritis, Usher's Syndrome, Leber's Congenital Amaurosis, Cone-Rod Dystrophy, Cone Dystrophy, Choroideremia and Gyrate Atrophy, Central Retinal Artery Occlusion, Central Retinal Vein Occlusion, Branch Retinal Artery Occlusion, Branch Retinal Vein Occlusion, Central Serous Chorioretinopathy, Cystoid Macular Edema, Ocular Histoplasmosis, Ocular Toxoplasmosis and Retinopathy of Prematurity.

Figure 4:
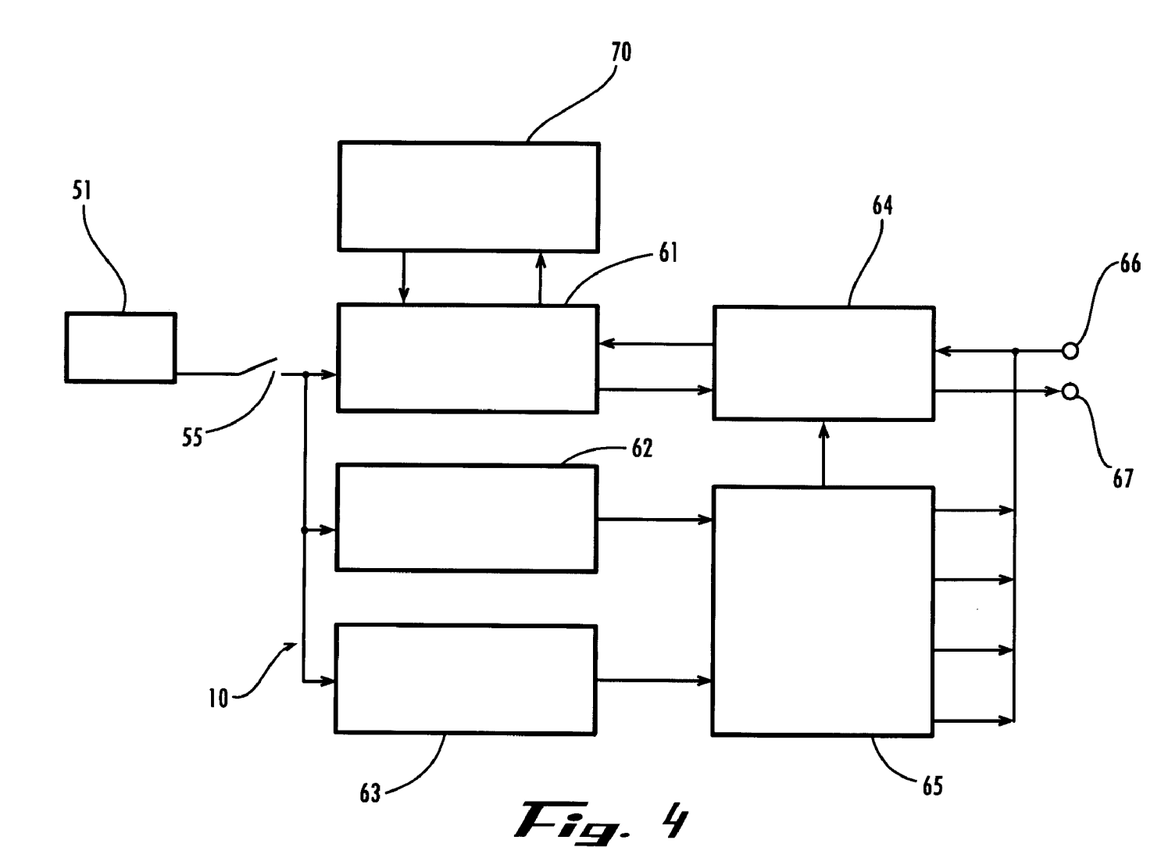
FIG. 4 is a block diagram of the of the microcurrent stimulation apparatus shown in FIG. 1 in accordance with an embodiment of the present invention.

FIG. 4 is a block diagram of the electrical components for an embodiment of the microcurrent stimulation apparatus (10) as seen in FIG. 1. A more complete description of electrical components of one embodiment is shown in the circuit diagram in FIG. 5A. There is a direct current power supply (51), which may be, for example, a nine-volt battery or household current adapter configured to supply nine volts to a connection or jack provided on the microcurrent stimulation apparatus (10). Current flows through an on/off switch (55) to voltage converter (61) to a regulator (62) and to an oscillator (63). Current flows from the regulator (62) and oscillator (63) to a frequency divider (65). A constant current source (64) receives current from the frequency divider (63) and from the voltage converter (61) and passes current from the constant current source to a first electrode (67). A circuit is completed from the first electrode (67) through the patient (not shown) to a second electrode (66). Current returns to the constant current source (67) to the voltage converter (61) through an amplitude control (70) and then to the power source (51) to complete the circuit.

Figure 5A:
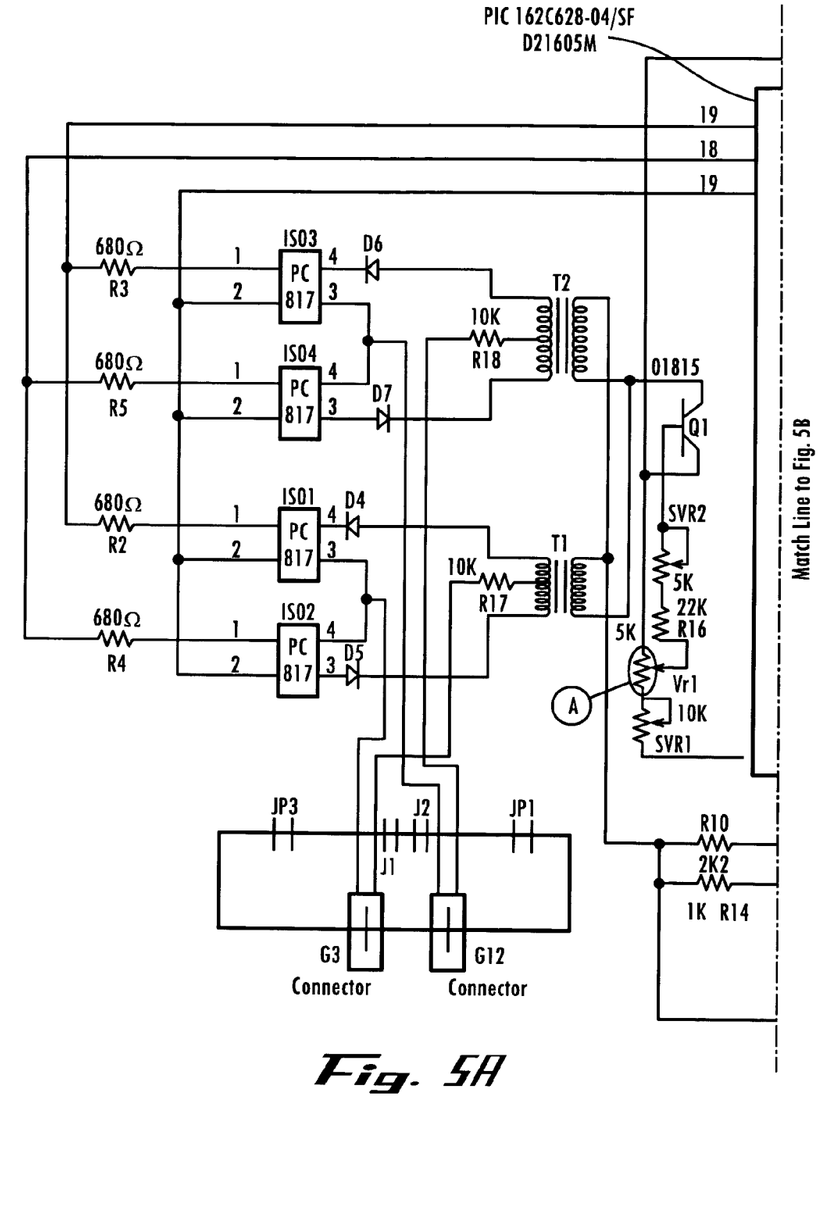
FIGS. 5A and 5B together comprise a schematic circuit diagram of the electrical circuitry of the MCS apparatus shown in FIG. 1.
Figure 5B:
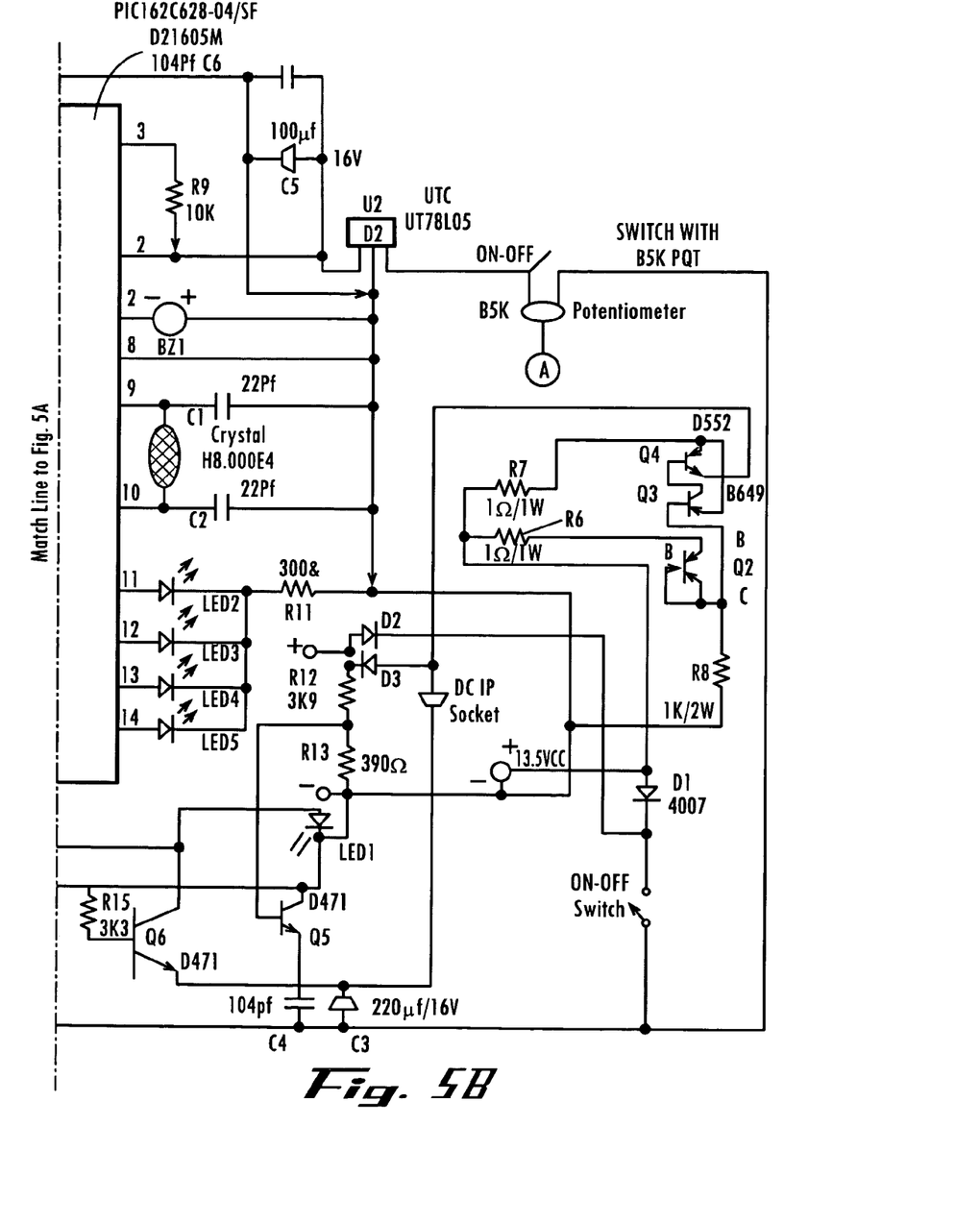

FIGS. 5A and 5B together represent a schematic circuit diagram of an embodiment of the electrical circuitry of the microcurrent stimulation apparatus (10). Standard symbols and terminology are used in labeling the circuit diagrams shown in FIGS. 5A and 5B. For ease of illustration, the potentiometer labeled "VR1" is shown in two places on the circuit diagram, but in the actual circuit there is only one VR1 potentiometer. This is indicated by the letter "A" with a circle around it and the arrow. This points to the same part. It will be understood that there is not two potentiometers, but only one from 5 kΩ to 85 kΩ resistance. A materials list is given below for the components used for this embodiment. It should be noted that the circuit shown in FIGS. 5A and 5B is only one of many possible ways to configure the microcurrent stimulation apparatus 10. Those skilled in the art will understand, in view of the description provided herein, the manner in which other circuit configurations can be created to perform same functions.

In accordance with this embodiment, four high-density photocoupler chips are employed. One chip that has been found to work in practice is manufactured by the Sharp Company and assigned product #PC817X. One chip is a programmable read only memory chip. One chip that has been found to work in practice is manufactured by Microchip. It is a 28 Pin, 8 Bit Micro Controller Chip and is assigned part #PIC16C628-04. This chip is equipped with timers, data memory, and other features required to produce and control appropriate microcurrent output and polarity. It will be appreciated by one of skill in the art that such standard things as diodes, resistors, capacitors, transformers, transistor switches and the like, which appear on the circuit diagram, can be varied without departing from the invention, which is to produce microcurrents with specified waveforms and carrier frequencies timed in a way to maximize the benefit and to induce patient compliance.

MATERIALS LIST

RESISTORS $R_1$ - JUMPER WIRE
(no resistor)
$R_2$ - 680 Ω
$R_3$ - 680 Ω
$R_4$ - 680 Ω
$R_5$ - 680 Ω
$R_6$ - 1 Ω/1 W
$R_7$ - 1 Ω/1 W
$R_8$ - 1 K/2 W
$R_9$ - 10 KΩ
$R_{10}$ - 2 K2
$R_{11}$ - 330 Ω
$R_{12}$ - 3 K9
$R_{13}$ - 390 Ω
$R_{14}$ - 1 KΩ
$R_{15}$ - 3 K3
$R_{16}$ - 22 kΩ
$R_{17}$ - 10 kΩ
$R_{18}$ - 10 kΩ

DIODES $D_1$ - 4007
$D_2$ - 4007
$D_3$ - 4007
$D_4$ - 4148
$D_5$ - 4148
$D_6$ - 4148
$D_7$ - 4148

BUZZER

BZ1 - 080
ON-OFF Switch

CAPACITORS $C_1$ - 22 pf
$C_2$ - 22 pf
$C_3$ - 220 μf/16 v

-continued

MATERIALS LIST $C_4$ - 104 pf
$C_5$ - 100 μf/16 v
$C_6$ - 104 pf

TRANSISTORS $Q_1$ - C1815
$Q_2$ - B649
$Q_3$ - B649
$Q_4$ - DB82
$Q_5$ - D471
$Q_6$ - D471

INTEGRATED CIRCUIT CHIPS

IS01 - PC817
IS02 - PC817
IS03 - PC817

LEDS $LED_1$ - Dipole LED
$LED_2$ - Green LED 5 mm
$LED_3$ - Green LED 5 mm
$LED_4$ - Green LED 5 mm
$LED_5$ - Green LED 5 mm

CRYSTAL OSCILLATOR-

H8.000E4

2 TRANSFORMERS

POT (VRI) 5 k (85 k)
PRESET VARIABLE
RESISTANCE

SVRI - 103 (10 k)
SVR2 - 503 (50 k)
ON-OFF Switch

Figure 6:
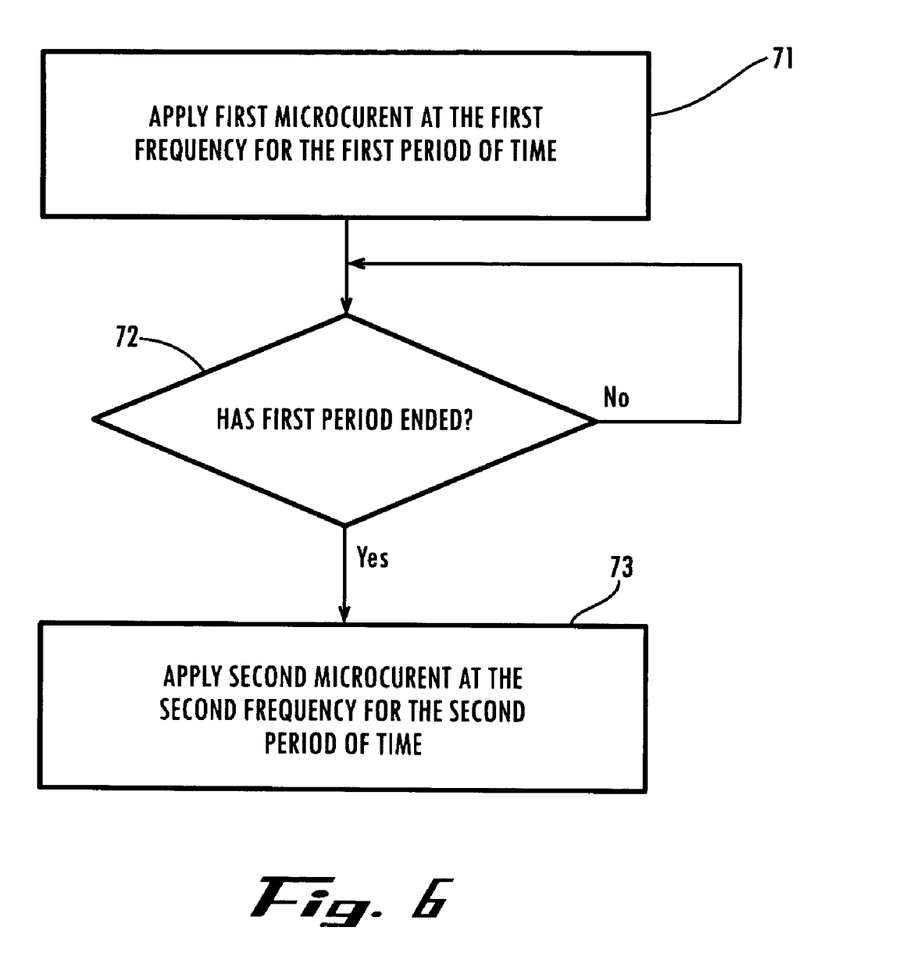
FIG. 6 is a flow chart illustrating the method of the present invention in accordance with an embodiment.

FIG. 6 is a flow chart of the method of the present invention in accordance with an embodiment for applying microcurrent to the ocular tissue at different frequencies for different periods of time. At least two microcurrent signals that are different in modulation frequency are applied to the ocular tissue for particular periods of time. The term "modulation frequency" denotes the beat frequency that is superimposed onto the carrier frequency, which preferably is between 10,000 and 20,000 Hz. A first microcurrent signal at a first modulation frequency is applied to the ocular tissue for a first period of time, as indicated by block 71. When a determinations is made that the first time period has ended, as indicated by block 72, at least a second microcurrent signal at a second modulation frequency, which is lower than the first modulation frequency, is applied to the ocular tissue for a second period of time, as indicated by block 73. The second period of time is greater than the first period of time.

As stated above, in accordance with the present invention, it has been determined that as the modulation frequency of the microcurrent signal decreases, the duration of the time period during which the signal is applied should be increased. It has also been determined that the sequence of modulation frequencies should start with a higher frequency and change to successively lower frequencies. Preferably, the modulation frequency ranges from approximately 400 Hz to approximately 0.1 Hz., although the invention is not limited to this particular range of frequencies.

In accordance with the preferred embodiment, at least three, but preferably four different microcurrent signals are applied to the ocular tissue in a particular sequence in which each subsequently applied signal in the sequence is lower in frequency than the previously applied signal. In accordance with this embodiment, each signal is applied for a longer period of time than the previously applied signal. One particular sequence that has produced excellent results is as follows. A first microcurrent signal having a first modulation frequency more than 200 Hz but less than or equal to 300 Hz is applied for a period from 1 second up to 120 seconds. A second microcurrent signal having a second modulation frequency more than 10 Hz but less than or equal to 200 Hz is then applied for a period from 1 second up to 240 seconds. A third microcurrent signal having a third modulation frequency more than 1 Hz but less than or equal to 10 Hz is then applied for a period from 10 seconds up to 800 seconds. A fourth microcurrent signal having a fourth modulation frequency greater than 0.1 Hz but less than or equal to 1 Hz is then applied for a period from 10 seconds up to 500 seconds.

It should be noted that the present invention has been described with reference to particular embodiments and that the invention is not limited to these embodiments. Those skilled in the art will understand the manner in which the embodiments described herein can be modified without deviating from the scope of the invention. For example, although particular designs for the electrode pad and the goggles have been described herein and shown in the drawings, the invention is not limited to any particular device or mechanism for applying the microcurrent to the ocular tissue. The electrode pad and goggles are merely examples of designs that are well suited for this purpose. As stated above, the invention is not limited to any particular circuit configurations for generating the microcurrents, waveforms and frequencies. Likewise, the present invention is not limited with respect to the manner in which the sequence of frequencies for particular time periods are selected or the manner in which the sequencing is controlled.

What is claimed is:

1. A microcurrent stimulation (MCS) kit comprising:
    an MCS apparatus comprising:
    an electrical circuit configured to generate a microcurrent signal having a particular carrier frequency modulated by one of at least first and second modulation frequencies;
    controller logic in communication with the electrical circuit, the controller logic being configured to control which of at least the first and second modulation frequencies are superimposed onto the carrier frequency and to control first and second time periods during which the first and second modulation frequencies, respectively, are superimposed onto the carrier frequency, the first modulation frequency being greater than the second modulation frequency and the first time period being shorter than the second time period, the second time period commencing upon expiration of the first time period;
    goggles comprising a microcurrent conductor configuration configured to receive the microcurrent signal generated by the electrical circuit and to apply the microcurrent signal to ocular tissue of the user;
    at least a first positive electrode connected on a first end thereof to a positive terminal of the electrical circuit, the first positive electrode having a second end electrically coupled to the microcurrent conductor configuration of the goggles for providing the microcurrent signal generated by the electrical circuit to the microcurrent conductor configuration of the goggles; and
    at least a second electrode connected on a first end thereof to a negative terminal of the electrical circuit, the first negative electrode having a second end configured to be placed in contact with a location on the user's body.

2. An apparatus for applying a microcurrent signal to ocular tissue of a user to perform microcurrent stimulation (MCS) therapy, the apparatus comprising:
    an electrical microcurrent signal generation circuit configured to generate an electrical microcurrent signal; and
    goggles configured to receive the microcurrent signal from the electrical microcurrent generation circuit and to provide the microcurrent signal to at least first and second electrodes of the goggles, the first electrode having a first end connected to a first terminal of the signal generation circuit and a second end connected to the goggles for delivering the microcurrent signal to the goggles, the second electrodes having a first end connected to a second terminal of the signal generation circuit and a second end configured to be placed in contact with a location on a user's body.

3. A kit for performing microcurrent stimulation (MCS) therapy that enables conditions of macular degeneration and other ocular diseases to be improved or at least stabilized, the kit comprising:
    pair of microcurrent stimulating devices for applying at least two microcurrent signals to ocular tissue of an eye of a user, the pair of microcurrent stimulating devices are designed to have a configuration of goggles, wherein the at least two microcurrent signals are different in modulation frequency, wherein the microcurrent stimulating device is capable of being operationally connected to a microcurrent stimulating device, wherein the microcurrent stimulating device is configured to be placed in direct contact with the eyelid of the eye or in proximity of the eye so that at least two microcurrent signals can be applied to the ocular tissue of the eye for particular periods of time.

* * * * *